US00PP33488P2

(12) United States Plant Patent
Snijder

(10) Patent No.: US PP33,488 P2
(45) Date of Patent: Sep. 14, 2021

(54) ***PELARGONIUM* PLANT NAMED 'PECZ0022'**

(50) Latin Name: *Pelargonium interspecific*
Varietal Denomination: PECZ0022

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/064,621

(22) Filed: Oct. 7, 2020

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
See application file for complete search history.

*Primary Examiner* — Susan McCormick Ewoldt
(74) *Attorney, Agent, or Firm* — Dale Skalla

(57) ABSTRACT

A new *Pelargonium* plant named 'PECZ0022' particularly distinguished by white colored inflorescences with semi-double florets, held above dark green foliage, on a vigorous upright plant.

1 Drawing Sheet

Latin name of the genus and species of the plant claimed: *Pelargonium interspecific.*

Varietal denomination: 'PECZ0022'.

BACKGROUND OF THE NEW PLANT

The present invention comprises a new *Pelargonium*, botanically known as *Pelargonium interspecific*, and hereinafter referred to by the variety name 'PECZ0022'.

'PECZ0022' is a product of a planned breeding program. The new cultivar 'PECZ0022' has white colored inflorescences with semi-double florets, held above dark green foliage, on a vigorous upright plant.

'PECZ0022' originates from a self-pollination made in July 2015, in a greenhouse in Enkhuizen, The Netherlands. The female parent was an unpatented plant of *P. interspecific* parentage identified as 'PEZ-BA7041-02' with light pink and larger florets, later flowering and poorer branching when compared to 'PECZ0022'.

The male parent was an unpatented plant of *P. interspecific* parentage identified as 'PEZ-BA7041-02' with light pink larger florets, later flowering and poorer branching when compared to 'PECZ0022'. The resultant seed was sown in December 2015.

'PECZ0022' was selected as one flowering plant within the progeny of the stated cross in May 2016 in a greenhouse in Enkhuizen.

The first act of asexual reproduction of 'PECZ0022' was accomplished when vegetative cuttings were propagated from the initial selection in June 2016 in a greenhouse in Enkhuizen, The Netherlands.

BRIEF SUMMARY OF INVENTION

Horticultural examination of plants grown from cuttings of the plant initiated in August 2016 in Enkhuizen, The Netherlands and continuing thereafter, has demonstrated that the combination of characteristics as herein disclosed for 'PECZ0022' are firmly fixed and are retained through successive generations of asexual reproduction.

'PECZ0022' has not been observed under all possible environmental conditions. The phenotype may vary significantly with variations in environment such as temperature, light intensity, and day length.

A Plant Breeder's Right for this cultivar has not yet been applied for. 'PECZ0022' has not been made publicly available prior to the effective filing date of this application, notwithstanding any disclosure that may have been made less than one year prior to the effective filing date of this application by the inventor or another who obtained 'PECZ0022' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PECZ0022' with colors being as true as possible with an illustration of this type.

Figure 1:
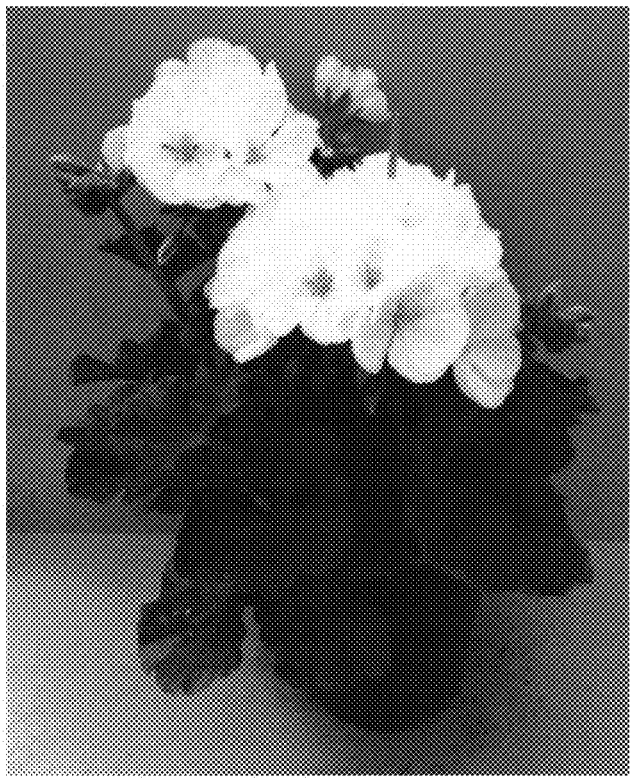
Figure 2:
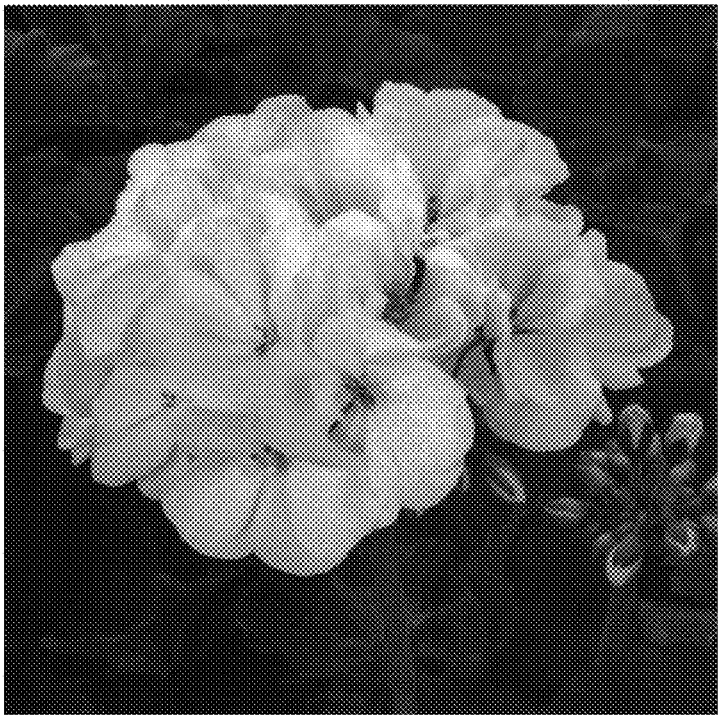

The photographic drawings show in FIG. 1, one plant of the new variety and in FIG. 2, a close-up of an inflorescence.

DETAILED BOTANICAL DESCRIPTION

The plant descriptions and measurements were taken in Enkhuizen, The Netherlands in early June 2020 under natural light. These plants were approximately 16 weeks old and were grown in a 12 cm pots, in a greenhouse trial. The plant shown in the photograph was about 16 weeks old growing in a 12 cm pot in a greenhouse. The photograph was taken in April 2020.

Color references are made to The Royal Horticultural Society Colour Chart (R.H.S.) 2001.

TABLE 1

DIFFERENCES BETWEEN THE NEW VARIETY 'PECZ0022' AND A MOST SIMILAR VARIETY

| | 'PECZ0022' | 'ZONFIWIT' (U.S. Plant Pat. No. 21,188) |
|---|---|---|
| Pollen amount: | Scarce | Abundant |
| Leaf size: | Larger | Smaller |

Plant:
*Form, growth and habit.*—Upright.
*Plant height.*—15.5-18 cm.
*Plant height (inflorescence included).*—18-22.5 cm.
*Plant width.*—17-20 cm.

Roots:
*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:
*Variegation.*—Absent.
*Immature leaf, color upper surface.*—Closest to RHS 137B.
*Immature leaf, lower surface.*—Closest to RHS 138B.
*Mature leaf, color upper surface.*—Closest to RHS 137A.
*Mature leaf, color lower surface.*—Closest to RHS 138B.
*Length.*—7-8 cm.
*Width.*—7.5-9 cm.
*Shape.*—Cordate.
*Base shape.*—Cordate.
*Apex shape.*—Acute.
*Margin.*—Slightly dentate.
*Texture upper side.*—Hirsute.
*Texture lower side.*—Hirsute.
*Leaf zonation color.*—None.
*Color of veins, upper surface.*—RHS 137A, largely indistinct.
*Color of veins, lower surface.*—RHS 144B, becoming indistinct.
*Pattern of veining.*—Palmate.
*Petiole color.*—RHS 143B.
*Petiole length.*—6-8 cm.
*Diameter of petiole.*—0.2 cm.
*Texture.*—Pilose, hirsute, glandular hairs.

Stem:
*Number of branches.*—3-8.
*Color of stem.*—Close to RHS 143B.
*Length of stem.*—8-15 cm.
*Diameter.*—0.5 cm.
*Length of internodes.*—1-4 cm.
*Texture.*—Sparsely hirsute, pilose, glandular hairs.

Peduncle:
*Color of peduncle.*—RHS 144A.
*Length of peduncle.*—11-19 cm.
*Peduncle diameter.*—0.3-0.5 cm.
*Texture.*—Hirsute, glandular hairs.

Pedicel:
*Color of pedicel.*—RHS N144A.
*Length of pedicel.*—2.8-3.4 cm.
*Diameter of pedicel.*—0.15-0.2 cm.
*Texture.*—Sparsely pilose, glandular hairs.

Bud (just before opening):
*Color.*—RHS 145C.
*Length.*—1.7-2.2 cm.
*Width.*—0.8-1.3 cm.
*Shape.*—Elliptical.

Inflorescence:
*Type.*—Umbel; semi-spherical or nearly semi-spherical.
*Lastingness of individual flowers.*—7-9 days at 18° C. temperature.
*Number of inflorescences per plant.*—3-8, with 1-5 immature umbels in various stages.
*Fragrance.*—None.
*Umbel diameter.*—9-15 cm.
*Umbel depth.*—7-10 cm.

Corolla:
*Form.*—Semi-double.
*Number of petals.*—6-10.
*Diameter of flower.*—4-5.5 cm.
*Depth of flower.*—1.5-2 cm.
*Color upper petals, upper surface.*—Whiter than RHS N155A.
*Color upper petals, lower surface.*—Whiter than RHS N155A.
*Length of upper petals.*—2.5-3 cm.
*Width of upper petals.*—2-2.2 cm.
*Color lower petals, upper surface.*—Whiter than RHS N155A.
*Color lower petals, lower surface.*—Whiter than RHS N155A.
*Length of lower petals.*—2.4-2.6 cm.
*Width of lower petals.*—2-2.2 cm, petaloids variably smaller smaller and with variable shape.
*Petal shape.*—Obovate to spathulate.
*Apex shape.*—Rounded.
*Margin.*—Entire.
*Base.*—Attenuate.
*Petal texture.*—Papillose on both surfaces.

Calyx:
*Number of sepals.*—5.
*Color of sepals.*—RHS 144C.
*Length of sepals.*—1-1.4 cm.
*Width of sepals.*—0.2-0.4 cm.
*Sepal shape.*—Lanceolate to linear.
*Apex shape.*—Acute.
*Margins.*—Mostly fused.
*Texture, upper surface.*—Glabrous.
*Lower surface.*—Glandular hairs, hirsute.

Reproductive organs:

Gynoecium:
*Pistil.*—RHS 145A.
*Length.*—0.8-0.9 cm.
*Style color.*—RHS 145A.
*Style length.*—0.3-0.4 cm.
*Stigma color.*—RHS 145A.
*Ovary color.*—RHS 144A.
*Ovary length.*—0.4-0.6 cm.
*Ovary diameter.*—0.2 cm.

Androecium:
*Number of stamens.*—6-9 with 1-5 staminoids.
*Color of filaments.*—Whiter than RHS 157D.
*Length filaments.*—0.5-0.8 cm.
*Anther color.*—RHS 171D.

*Length of anthers*.—0.2 cm.
*Color of pollen*.—RHS N169C.
*Pollen amount*.—Scarce.
*Fertility/seed set*.—Has not been determined to date.
*Disease/pest resistance*.—Has not been determined to date.

What is claimed is:

1. A new and distinct variety of *Pelargonium* plant named 'PECZ0022' substantially as illustrated and described herein.

* * * * *